ical Patent [19]

Kendal et al.

[11] Patent Number: 5,290,686
[45] Date of Patent: Mar. 1, 1994

[54] EXPRESSION OF INFLUENZA A M2 PROTEIN IN BACULOVIRUS

[75] Inventors: Alan P. Kendal; Renee Black, both of Atlanta; Paul A. Rota, Decatur, all of Ga.

[73] Assignee: The United States of America as represented by the Department of Health and Human Services, Washington, D.C.

[21] Appl. No.: 738,032

[22] Filed: Jul. 31, 1991

[51] Int. Cl.$^5$ .......................... C12N 5/10; C12P 21/02
[52] U.S. Cl. ................................ 435/69.1; 435/320.1; 435/172.3; 435/240.2
[58] Field of Search .................... 435/69.3, 320.1, 240.2

[56] References Cited

PUBLICATIONS

Luckow and Summers, 1988, Bio/Technology, vol. 6 pp. 47–55.
Matsuura et al, Journal of General Virology, 68, 1233–1250 (1987).
Cox et al, Virology 167, 554–567 (1988).
Sugrue et al, The EMBO Journal 9; 3469–3476, (1990).
Sugrue et al, Virology 180:617–624 (1991).
Lamb, R. A., et al., "Influenza Virus M2 Protein Is an Integral Membrane Protein Expressed on the Infected-Cell Surface," *Cell* 40:627–633 (1985).
Schmaljohn, C. S., et al., "Baculovirus Expression of the Small Genome Segment of Hantaan Virus and Potential Use of the Expressed Nucleocapsid Protein as a Diagnostic Antigen," *J. Gen Virol.* 69:777–786 (1988).
Roitt, I., "Essential Immunology," Fourth Edition, Blackwell Scientific Publications, 1980, pp. 144–150.
Zebedee, S. L., et al., "Characterization of the Influenza Virus $M_2$ Integral Membrane Protein and Expression at the Infected–Cell Surface from Cloned cDNA," *J. Virol.* 56(2):502–511 (Nov. 1985).

*Primary Examiner*—Richard A. Schwartz
*Assistant Examiner*—David Guzo
*Attorney, Agent, or Firm*—Townsend and Townsend Khourie and Crew

[57] ABSTRACT

The present invention relates to baculovirus-expressed influenza antigens, in particular, to the influenza A membrane protein, M2, expressed from *Autographa Californica* nuclear polyhedrosis virus (AcNPV). The present invention further relates to a method to increase the yield of baculovirus-expressed M2 proteins in host cells by culturing the recombinant baculovirus infected host cells with an amantadine-like drug. Other aspect of the present invention relate to the use of baculovirus-expressed M2 proteins in reproducible and routine assays for the seradiagnosis of influenza A virus infections as an alternative to the more burdensome complement fixation and hemagglutination tests.

12 Claims, 8 Drawing Sheets

PRIMERS FOR THE A/AA/6/60 M2 GENE FOR PCR INCLUDING
BamH1 AND BglII SITES FOR INSERTION INTO THE YM1 VECTOR
FOR BACULOVIRUS.

PRIMER M2F mRNA SENSE

5' GATCGGATCCAAGATGAGTCTTCTA 3' 25 mer
    4  BamH1   15
        6

PRIMER M2R REVERSE -COMPLEMENT

5' GATCAGATCTTTACTCCAGCTCTAT 3' 25 mer
    4  BglII   15
        6

*FIG. 1.*

EXPRESSION OF INFLUENZA A M2 PROTEIN IN BACULOVIRUS

BACKGROUND OF THE INVENTION

1. Field of the Invention

The present invention relates to baculovirus-expressed influenza antigens, in particular, to the influenza A membrane protein, M2 expressed from *Autographa Californica* nuclear polyhedrosis virus (AcNPV). The invention further relates to immunoassays for the detection of influenza viral infections and to the use of such protein in vaccines against influenza A.

2. Background Information

The M2-protein of influenza A viruses is a membrane-spanning protein. It is found within membranes of virus-infected cells (R.A. Lamb and P.W. Choppin *Virology* 112:729-737 (1981) ; R.A. Lamb et al, *Cell* 40:627-633 (1985)). A small number of M2 proteins are also present in virus particles (S.L. Zebedee and R.A. Lamb *J. Virol.* 62:2762-2772 (1988)). Mutations occur in the transmembrane region of M2 protein present in viruses selected in vitro or in vivo to be resistant to the anti-viral agents amantadine and rimantadine (A.J. Hay et al, *EMBO J.* 4:3021-3024 (1985); W.J. Bean et al, *J. Infect. Dis.* 159:1050-1056 (1989)). One model for the function of M2 protein is that it possess ion-channel activity, which is inhibited by amantadine-like agents (R.J. Sugrue et al, *EMBO J.* 9:3469-3476, 1990; R.I. Sugrue et al, *Virology* 180:617-624 (1991). Amantadine-like agents include amantadine and various N-alkyl derivatives of amantadine which inhibit neuromuscular transmission by interacting with the ion channel of the nicotinic acetylcholine receptor and competitively inhibit the binding of other channel blockers, phencyclidine and histrionicotoxin, to the receptor. Although under some circumstances amantadine may indirectly interfere with the correct processing of the cleaved hemagglutinin of the Rostock strain of Fowl Plague Virus (R.J. Sugrue et al, *EMBO J.* 9:3469-3476 (1990)), it is a general rule that amantadine-like agents inhibit an early event in the replication of influenza A viruses, which occurs prior to transcription and translation of the genome of infecting virions (Hay et al, (1985); A.J. Hay and M.C. Zambon, Multiple actions of amantadine against influenza viruses. In Becker Y. (ed) Antiviral drugs and interferon: the molecular basis of their activity. Martinus Niihoff Publishing, Boston MA, pp. 301-315, (1984)) including the Rostock virus. Hence, even the small number of M2 proteins within virus particles are presumably involved in the early event blocked by amantadine. However, direct evidence about the function of M2 protein or its interaction with amantadine is lacking.

Since the M2 protein is conserved among various strains of influenza A virus, it may have potential for use as an influenza vaccine. It has recently been demonstrated that mice receiving passively transferred monoclonal antibody to M2 had lower liters of influenza virus in their lungs after intranasal challenge with live influenza virus (J. Treanor et al, *J. Virol.* 64:1375-1377 (1990)).

To facilitate structure-function studies of M2 protein, as well as to develop reagents needed for immunological studies, the present invention provides, in one particular aspect, the M2 gene of influenza A virus cloned into a recombinant baculovirus allowing its expression in insect cells.

Viral antigens produced by recombinant DNA expression systems can provide an inexhaustible source of chemically defined material for use in serodiagnostic assays, experimental vaccines, and fundamental research. These techniques also eliminate the costs and potential hazards in the large-scale cultivation of pathogenic viruses. For example, the use of baculovirus-expressed Hantaan virus nucleoprotein as a diagnostic antigen has been reported recently (Schmaljohn et al, *Journal of General Virology* 69:777-786 (1988)).

The recently developed eucaryotic expression system using recombinant baculovirus, *Autographa californica* nuclear polyhedrosis virus (AcNPV), should be useful for producing antigens for immunoassays for the serologic diagnosis of viral infections (Luckow et al, *Biotechnology* 6:47-55 (1987) Infection of insect cells (*Spodoptera frugiperda*) with such recombinant baculoviruses allows for the production of large amounts of antigen (R.D. Possee, *Virus Research* 5:43-59 (1986)). In addition, the baculovirus system has other important advantages over the commonly used methods of producing viral antigens. For example, with the baculovirus system the viral antigens are produced in cells that do not contain antigens that cross-react with antibodies in most human serum. Therefore, the purification of the antigen that is required for proteins expressed in bacterial and yeast expression systems may not be required. Baculoviruses do not infect humans and can therefore be safely handled in large quantities.

SUMMARY OF THE INVENTION

It is an object of the present invention to provide a less costly, easier and safer means of producing influenza A M2 protein. M2 is very difficult to purify from influenza-infected cells.

It is another object of the present invention to provide baculovirus-expressed M2 from influenza A for use in serodiagnostic assays for influenza virus.

It is a further object of the present invention to provide serodiagnostic assays for the detection and diagnosis of influenza A viral infections.

Various other objects and advantages of the present invention will become apparent from the drawings and the following detailed description of the invention.

In one embodiment, the present invention relates to a DNA construct comprising a DNA segment encoding M2 protein influenza A; and a vector comprising a polyhedron gene promoter from a baculovirus, baculovirus flanking sequences and a bacterial origin of replication. The DNA segment of the construct is operably linked to the polyhedron gene promoter of the vector.

In another embodiment, the present invention relates to recombinant baculovirus and to host cells infected therewith. Recombinant baculovirus to which the present invention relates encode a M2 of influenza A virus. Host insect cells of the present invention are infected with a recombinant baculovirus in a manner allowing the expression of the M2 encoded in the baculovirus.

In another embodiment, the present invention relates to baculovirus-expressed influenza A M2 and to a method of producing the baculovirus-expressed influenza A M2. Baculovirus-expressed influenza A M2 protein is produced by culturing host insect cells of the present invention in the presence of amantadine-like agents in a manner allowing an increased yield of M2 protein, and subsequently extracting the M2 proteins from the cells.

In a further embodiment, the present invention relates to a bioassay for the diagnosis of influenza A in mammals comprising the steps of coating a surface with the baculovirus-expressed M2 protein of the present invention, contacting the coated surface with a biological sample from an animal suspected of having influenza A, and detecting the presence or absence of a complex formed between the protein and antibodies specific thereto present in the biological sample. The present invention also relates to diagnostic kits comprising the baculovirus-expressed M2 and ancillary reagents suitable for use in detecting the presence or absence of antibodies to the protein in a biological sample.

In yet a further embodiment, the present invention relates to a vaccine for animals against influenza A virus. The vaccine comprises the baculovirus-expressed membrane protein of the present invention, in an amount sufficient to induce immunization against the virus, and a pharmaceutically acceptable carrier.

BRIEF DESCRIPTION OF THE DRAWINGS

FIG. 1 shows the primers used for the PCR amplification and cloning of the M2 gene from influenza A/Ann Arbor/6/60 virus. The sequence of the segment 7 of A/Ann Arbor/6/60 was previously determined by Cox et al, *Virology* 167:554–567 (1989)).

DETAILED DESCRIPTION OF THE INVENTION

Figure 2:
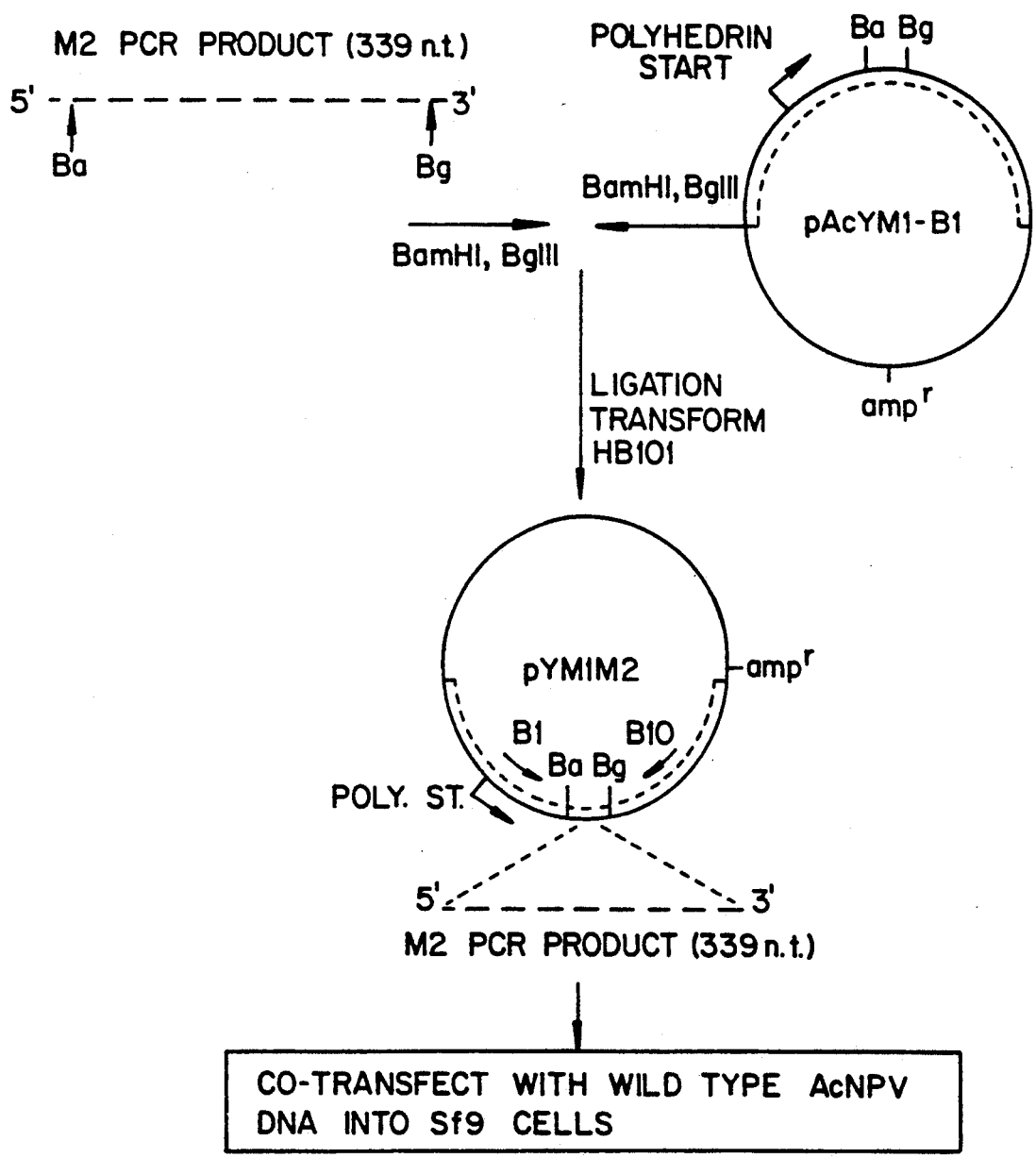
FIG. 2 shows the strategy used for cloning and expression of the influenza M2 gene in baculovirus. The M2 gene was amplified using PCR from CDNA prepared from total infected cell RNA. The PCR product was digested with the appropriate restriction endonucleases (BamHI and BglII) and inserted into the baculovirus transfer vector, pAcYM1B1, downstream of the polyhedron gene start site. (Ba, BamHI; Bg, BglII; B1, pAcYM1 forward sequencing primer; B10, pAcYM1 reverse sequencing primer; dotted line within plasmid circles indicates baculovirus DNA.)

The present invention relates to a system for expressing influenza A M2 protein utilizing baculovirus and to the proteins made therewith. M2 proteins to which the present invention relates react specifically with anti-influenza A antibodies and, therefore, can be used in serodiagnostic assays. The present invention provides an easier and safer means of producing influenza virus M2 and is less costly than current methods. For example, the present invention is safer than the isolation of M2 from whole virus as the recombinant viruses of the present invention are not infectious for mammals. In addition, the M2 antigens of the present invention do not need further costly purification in order to separate them from other proteins which react strongly with human serum. Such separation is necessary for M2 antigens produced in bacterial systems.

In one embodiment, the present invention relates to a DNA construct encoding a M2 antigen of an influenza virus. The DNA construct comprises a DNA segment encoding a M2 of an influenza A virus and a vector. The vector comprises the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoterM2 antigen combination is flanked on both sides by 200–300 base paris of baculovirus DNA (the flanking sequences). Suitable vectors for use in the present invention include, but are not limited to, pacym1.

To produce the DNA construct of the present invention, a CDNA clone encoding the full length M2 of an influenza A virus is obtained using methods known in the art, in this case, PCR amplification of M2 RNA.

The DNA construct of the present invention is used to generate recombinant baculoviruses. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encodes the full length influenza A M2. For example, an insect cell can be cotransfected or transfected separately with a DNA construct of the present invention and a functional baculovirus. Resulting recombinant baculoviruses can then be isolated and used to infect cells to effect production of the M2.

In another embodiment, the present invention relates to host insect cells, for example, *Spodoptera frugiperda* cells, producing a baculovirus-expressed influenza M2. Insect host cells infected with a recombinant baculovirus of the present invention and cultured under conditions allowing expression of the baculovirus-encoded M2 produce baculovirus-expressed M2 antigens. M2 thus produced is then extracted from the cells using methods known in the art. Further, it is contemplated that host cells can be stably transformed with the DNA constructs of the present invention.

In a further embodiment, the present invention relates to a method to increase the yield of the baculovirus-expressed M2 proteins in host insect cells, for example, *Spodoptera frugiperda*. The method contemplates culturing recombinant baculovirus infected host insect cells of the present invention with the amantadine-like drugs, for example, rimantidine, under conditions such that infected cells cultured with the drug yield increased concentrations of M2 protein in the cells.

It appears that M2 protein is highly toxic for insect cells when significant amounts of the M2 protein accumulate in the cells. A partial inhibition of this toxicity is found with the addition of amantadine-like agents that are putative inhibitors of ion-channel activity of M2 protein. Presumably the presence of the agents permit M2 protein to accumulate to higher concentrations intracellularly before its presumed cytotoxic effect is fully seen.

In another embodiment, the present invention relates to immunoassays for the diagnosis of influenza virus infections in animals. Using standard diagnostic protocols the baculovirus-expressed M2 of the present invention can be used to detect the presence of antibodies specific therefore in biological samples without undue experimentation. Because the M2 protein is type specific for influenza A viruses, its inclusion as an antigen in serodiagnostic tests may improve the efficiency and breadth of a application of such tests.

For example, by coating a solid surface such as a polystyrene microtitration plate, a slide or nylon or nitrocellulose membranes generated by immunoblot or Western blot, with the baculovirus-expressed M2 of the present invention and contacting the surfaced with a biological sample, such as serum, the presence or absence of antibodies to the influenza A can be detected. If antibodies are present in the sample, formation of antibody-protein complexes is effected. These complexes can be detected using standard methodologies known in the art.

The present invention further relates to diagnostic kits. The diagnostic kits of the present invention comprise the baculovirus-expressed M2 antigens of the present invention and ancillary reagents suitable for use in detecting the presence or absence of antibodies of the DNA constructs of the present invention necessary for production of the M2 and ancillary reagents. Availability of high yields of M2 protein may facilitate the capability of manufacturing diagnostic test kits.

In further embodiment, the present invention relates to vaccines for animals against influenza A infections. Antibodies against influenza can be raised by administering to an animal a vaccine comprising the baculovirus expressed M2 of the present invention in a pharmaceutically acceptable carrier or as a live recombinant virus vaccine. The baculovirus expressed M2 antigen is present in the vaccine in an amount sufficient to induce immunization which may be protective against the virus. Vaccines of the present invention can also include effective amounts of immunological adjuvants known to enhance an immune response.

In a further embodiment, the present invention relates to therapeutic methods that alter membrane function in the treatment of diseases and infections such as cancer, AIDS and neuronal diseases, for example.

The presumption of finding of high cytotoxicity of M2 protein raised interesting questions about the role of the protein in altering membrane functions. The M2 protein, which is a membrane spanning protein, may affect a membrane associated enzyme complex, or directly alter cell membrane functions such as controlling ion transport, transport of other critical molecules, conductance, or receptor molecules. Any such activity raises the possibility that M2 protein may have specific medical applications.

In the method contemplated by the present invention, the M2 protein or an expression system containing the M2 gene may be targeted against undesirable cells (for example, cancer cells, HIV-infected T cells and neuronal cells) by a specific delivery system, for example, liposomes or genetically recombinant viruses. Introduction of the M2 protein or expression of M2 may cause these cells to die. Controlling the effect by the use of amantadine, an approved human therapeutic drug, or amantadine-like drug may be important in such instances.

The following examples are given to further illustrate the present invention without being deemed limitative thereof.

EXAMPLES

The following materials/protocols are referred to in the Examples that follow.

Monoclonal Antibodies

Hybridoma cells producing an M2-specific monoclonal antibody were used according to Zeebedee et al., 1988. These cells (14C-2) were grown in Optimem with % fetal bovine serum and inoculated into pristane-primed Balb/C mice (6–32 $\times 10^5$ cells/mouse). The resulting ascites fluid was harvested and used as the source of anti-M2 monoclonal antibody for all FA, Western blot, and EIA tests.

cDNA Cloning of Influenza M2 Gene

RNA was purified from CV-1 cells 6 hours after infection with A/Ann Arbor/6/60 virus (m.o.i.=10). Cells were washed 3X with cold PBS and lysed in 5.8M guanidinium isothiocyanate, 50mm tris HCl (pH7.6), 10 mM EDTA, 2% sodium lauaryl sarkosinate, and 1% 2-mercaptoethanol. Lysates were centrifuged through a 5.7M CsCl cushion and the RNA pellet was collected as previously described (Maniatis et al, Molecular Cloning: A Laboratory Manual,. Cold Spring Harbor Laboratory, Cold Spring Harbor, N.Y. (1982)). RNA was further purified by phenol:chloroform extraction and concentrated by ethanol precipitation. Approximately 50µg of RNA was used in each sequencing reaction using M2 reverse message compliment primer (FIG. 1) to verify the presence of M2 MRNA. M2 CDNA was prepared from total infected cell RNA in a reaction containing 1, 5, or 10 µg RNA, 2.5X PCR buffer (Perkin Elmer-Cetus) 500 uM DTNP, 1µg M2R primer (FIG. 1), 20 U RNasin (Promega) and 20 U reverse transcriptase in a 50 µl reaction. After incubation at 42° C. for 40 minutes, 25 µl of the CDNA was added to 75 µl of PCR mix containing 1 µg M2F (FIG. 1) and 20 U Taq polymerase. PCR conditions were 94° C., 5 min.; 25 cycles of 94° C. 1 min., 50° C., 2 min., 72° C., 3 min; and 72° C. 5 min. 10 minutes. The PCR products were analyzed by electrophoresis on .8% agarose gels, followed by Southern blotting (Maniatis et al, 1982).

The M2 PCR products and the pAcYM1 vector, containing a unique BamHI BglII cloning sites were digested with restriction endonucleases BamHI and BglII and purified by agarose gel electrophoreses. Vector and insert were ligated and used to transform E. coli HB101 cells. Colonies were containing the M2 gene were identified by hybridization using a radiolabeled, M2-specific primer. Plasmid DNA from clone YM1/M2/19 was purified by CsCl centrifugation and sequenced using the B1 and B10 sequencing primers (FIG. 2). These oligonucleotide primers were designed to sequence the 5' and 3' ends of DNA fragments inserted into the multiple cloning site of pacYM1.

Construction of Recombinant Baculovirus

Plasmid DNA from YM1/M2/19 was co-transfected with wild type ACNPV DNA into SF9 cells using the CaCl method of M.D. Summers and G.E. Smith, A Manual of Methods for Baculovirus Vectors and Insect Cell Culture Procedures (1986). Six to 10 days after transfection M2 expression was detected by indirect immunofluorescent antibody on acetone-fixed cells using 14C-2 monoclonal antibody at a 1:20 dilution and (Tago) goat antimouse FITC conjugate. Recombinant baculovirus (Bac-M2) was purified by limiting dilution assay followed by plaque purification as described by Rota et al, *J. Gen. Virol.* 71: 1545–1554 (1990)).

Analysis of baculovirus Expressed M2 Protein

SF9 cells were seeded in chambered slides at 0.2ml cells/chamber. Cells were allowed to adhere overnight. The Bac-M2 virus was inoculated at several dilutions 50–100 µl/well and adsorbed 30 minutes and a total volume of 300 µ Hinks medium with 8% FBS was added. When the CPE was 25% to 50% complete, the medium was aspirated and the cells were washed with cold PBS at pH 6.5. For surface fluorescence cells were not allowed to dry and cold, fresh 2% paraformaldahyde in PBS pH 6.5 was added to cells and incubated 4° C. for 30 minutes. To determine internal fluorescence cells were allowed to dry and cold acetine was added to wells and incubated at 4° C. for 10 minutes. The cells were then incubated with the C14-2 monoclonal antibody to detect M2 protein. Bound Mab was detected using goat antimouse FITC-labelled IgG containing Evans Blue.

Lysates of SF9 cells infected with Bac-M2 were prepared in 10mM tris, 1 mm EDTA, with 2% Triton 100 and 0.5M KCl (Zebedee et al, *J. Virol.* 56:502–511 (1985)) and were subjected to electrophoresis on 20% SDS-PAGE gels containing 4M urea (R. Lamb et al, *Virology* 91:60–78 (1978)). Proteins were transferred to nitrocellulose filters for Western blot analysis using a semi-dry transblot cell. The M2 protein was detected with C14-2 monoclonal antibody and bound antibody detected with 125I-labeled Protein A and autoradiography.

EIA Procedure

To prepare antigen for EIA 0.1ml of infected SF9 cell sediment in 0.35 ml water was incubated at 37° C. and 0.05ml 10x alkaline glycine was added (10x glycine: 1M glycine in 1M NaCl; glycine/NaCl added to 1N NAOH pH 10). This mixture was sonicated and incubated at 37° C. for 30 minutes and the cell debris was pelleted. The M2 antigen containing supernatent was diluted in carbonate buffer pH 9.6 and used to coat polystyrene microtiter plates for EIA as previously described (Rota et al., 1990). Acute and convalescent phase human serum samples from individuals with used to confirmed antibody responses to influenza A. Serum samples were also analyzed by Western blot as described above.

EXAMPLE 1 cDNA Cloning and Expression of Influenza A M2 Protein in Insect Cells

Figure 3B:
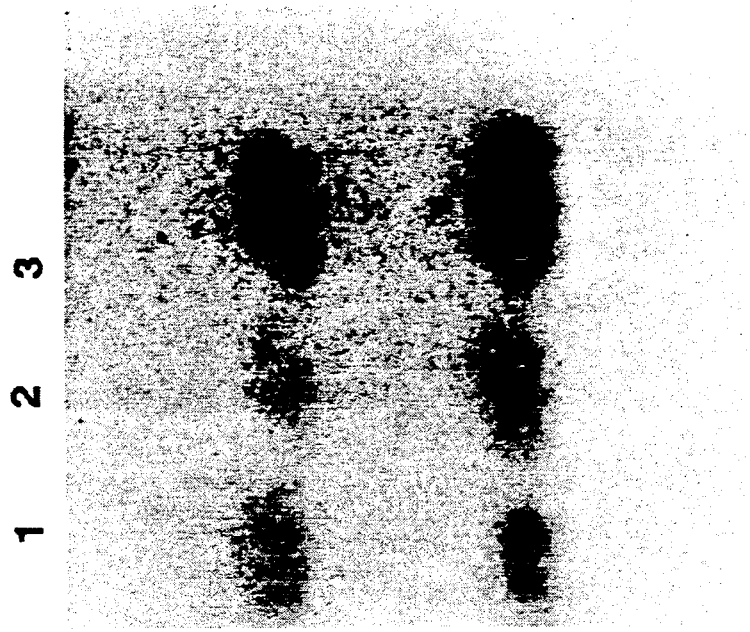
FIG. 3 demonstrates the PCR amplification of the influenza M2 gene. RNA was purified from CV-1 cells at 6 hours after infection with A/Ann Arbor/6/60 virus (m.o.i.=10). M2 CDNA was prepared from total RNA using reverse transcriptase and a primer specific for the 3' end of M2 MRNA (M2R see FIG. 1). PCR (25 cycles) was used to amplify the M2 CDNA using both M2R and M2F (FIG. 1) primers. Panel A: PCR products obtained after using 1μg (lane 1), 5μg (lane 2) or 10μg (lane 3) of infected cell RNA in the CDNA reaction. Positions of 1078 bp and 310 bp molecular weight markers are indicated. M2=315 bps; M1=1027. Panel B: Southern blot of the PCR products (panel A) after hybridization to a $^{32}$-P-labeled M-gene specific primer.
Figure 3A:
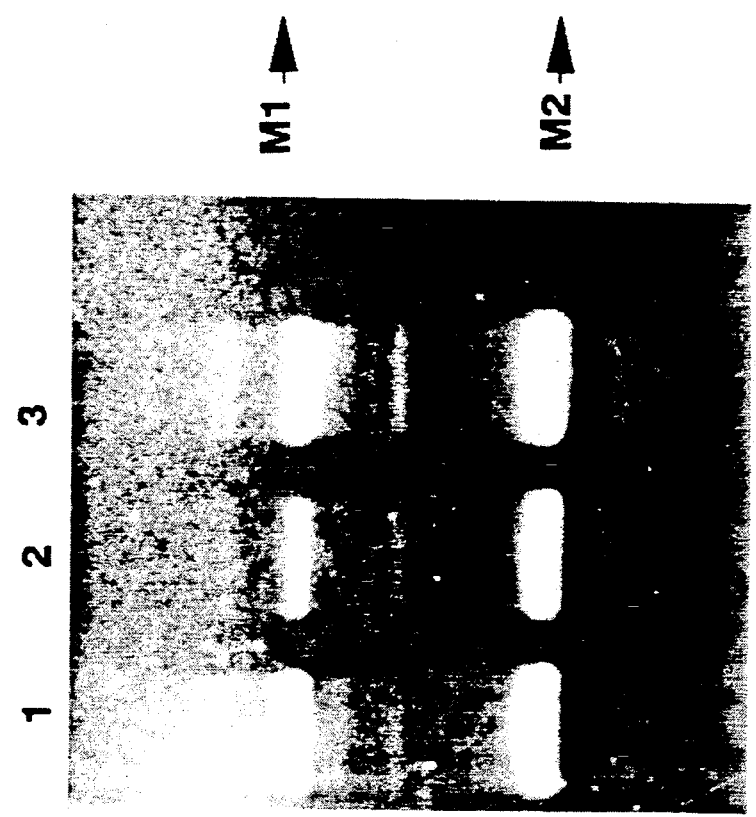

The M1 protein of influenza A is encoded by a collinear transcript whereas the M2 protein is translated from a spliced MRNA (R. Lamb et al, (1978)). Therefore, it was necessary to amplify the M2 gene as demonstrated by agarose gel and the Southern blot analysis of the PCR products (FIG. 3). The PCR product was digested with Hinfl to verify identity of the gene and to demonstrate the size of the M2 gene to be inserted.

Specifically constructed M2 primers with a BamHI restriction enzyme site on the forward primer and a BglII site on the reverse compliment primer facilitated the insertion of the PCR amplified M2 gene into the baculovirus transfer vector pAcYM1 (FIGS. 1 and 2). After sequencing with YM1/M2 with the B1 forward and B10 reverse primers of the YM1 vector it was found that the M2 gene was in the correct orientation relative to the polyhedron start site which begins at the BamHI site (Y. Matsuura et al, *Virology* 68: 1233-1250 (1987) The YM1/M2 plasmid was cotransfected with ACNPV DNA into SF9 cells to generate the recombinant baculovirus, Bac-M2, expressing the influenza M2 protein as described above.

Figures 4A, 4B:
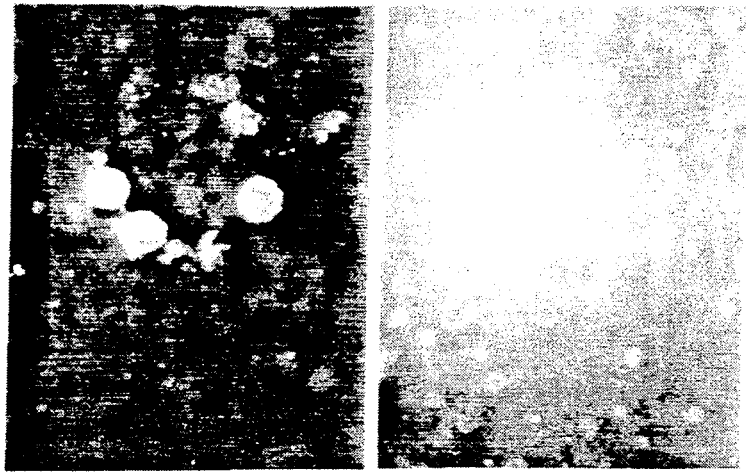
FIG. 4 shows an indirect immunofluorescence assay to detect influenza M2 protein in SF9 cells infected with recombinant baculovirus. Infected (A) or uninfected (B) SF9 cells were fixed with acetone and incubated with and M2-specific monoclonal antibody (14C2). Bound monoclonal antibody was detected using FITC-conjugated goat antimouse IgG. Counterstain was with Evans Blue. Magnification was 400X.

SF9 cells infected with the recombinant virus, Bac-M2, were analyzed by fluorescent antibody assay. These cells showed intense perinuclear fluorescence when incubated with monoclonal antibody specific for the M2 protein and stained with FITC conjugate (FIG. 4). Cells were also treated with 2% paraformaldahyde to detect surface fluorescence. Results indicated that the M2 was present on the cell membranes.

EXAMPLE 2

Analysis of Recombinant Baculovirus

Figure 5:
FIG. 5 shows a Western blot analysis of baculovirus-expressed influenza M2 protein. Lysates of SF9 cells infected with the recombinant baculovirus were prepared in 2% triton, 0.5M KCl and subjected to electrophoresis on 17% polyacrylamide gels containing 4M urea. M2 protein was detected using an M2-specific monoclonal antibody (14C2) and bound antibody was detected with $^{125}$-I protein A. Lane A: radiolabeled ($^{35}$S-cysteine) lysate of CV-1 cells infected with A/Ann Arbor/6/60 virus, lane B; non-radiolabeled lysate of CV-1 cells infected with A/Ann Arbor/6/60 virus, lanes C, D, and E: lysates of SF9 cells infected with the recombinant baculovirus expressing influenza M2 (lanes contained 400, 340 and 240 μg of protein, respectively), M2 is approximately 15000 kd in size; lane F: lysate of SF9 cells infected with a recombinant baculovirus expressing influenza nucleoprotein (340μg protein), lane G: lysate of uninfected SF9 cells.

Western blot analysis demonstrated that the recombinant M2 protein and the A/AA/6/60 M2 protein obtained from purified virus were identical in size and electrophoretic mobility when identified by anti-M2 monoclonal antibody (FIG. 5). The monoclonal antibody did not cross react with lysates prepared from uninfected Sf9 cells or with lysates from Sf9 cells infected with a recombinant baculovirus expressing the influenza B NP protein. These results indicated that Bac-M2 was producing a protein nearly identical to the M2 protein found in influenza A virus infected cells and that this recombinant M2 protein was being expressed at the cell surface.

EXAMPLE 3

Antigenic Reactivity of Baculovirus Expressed M2 Protein Antigens

Figure 7:
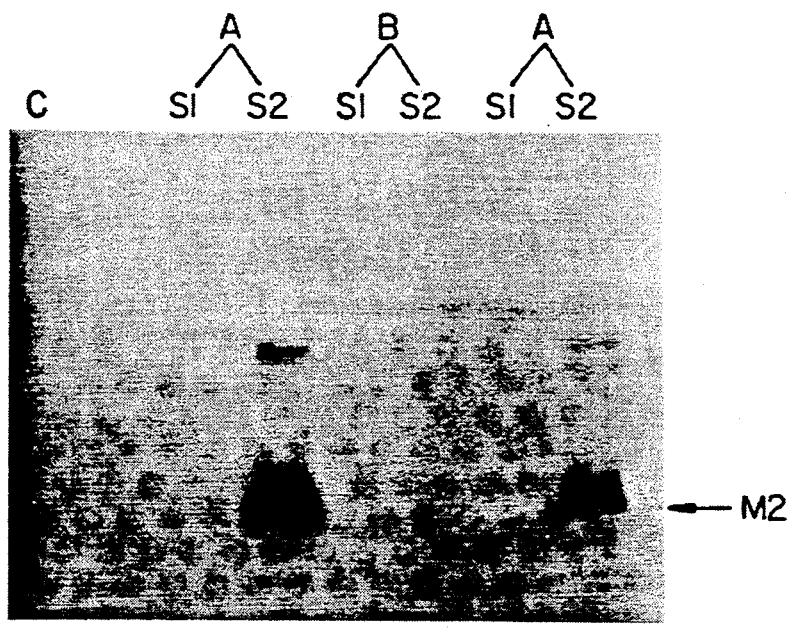
FIG. 7 shows the detection of M2-specific antibodies in human serum samples by Western blot. Lysates of SF9 cells infected with the recombinant baculovirus expressing M2 were subjected to SDS-PAGE and transferred to nylon filters as described in FIG. 5. Filters were incubated with acute (S1) or convalescent (S2) phase antiserum from patients with confirmed cases of either influenza A or influenza B. Bound antibody was detected as previously described. C=control lysate of mock cells infected with A/Ann Arbor/6/60 hybridized to 14C-2 Mab.
Figure 6:
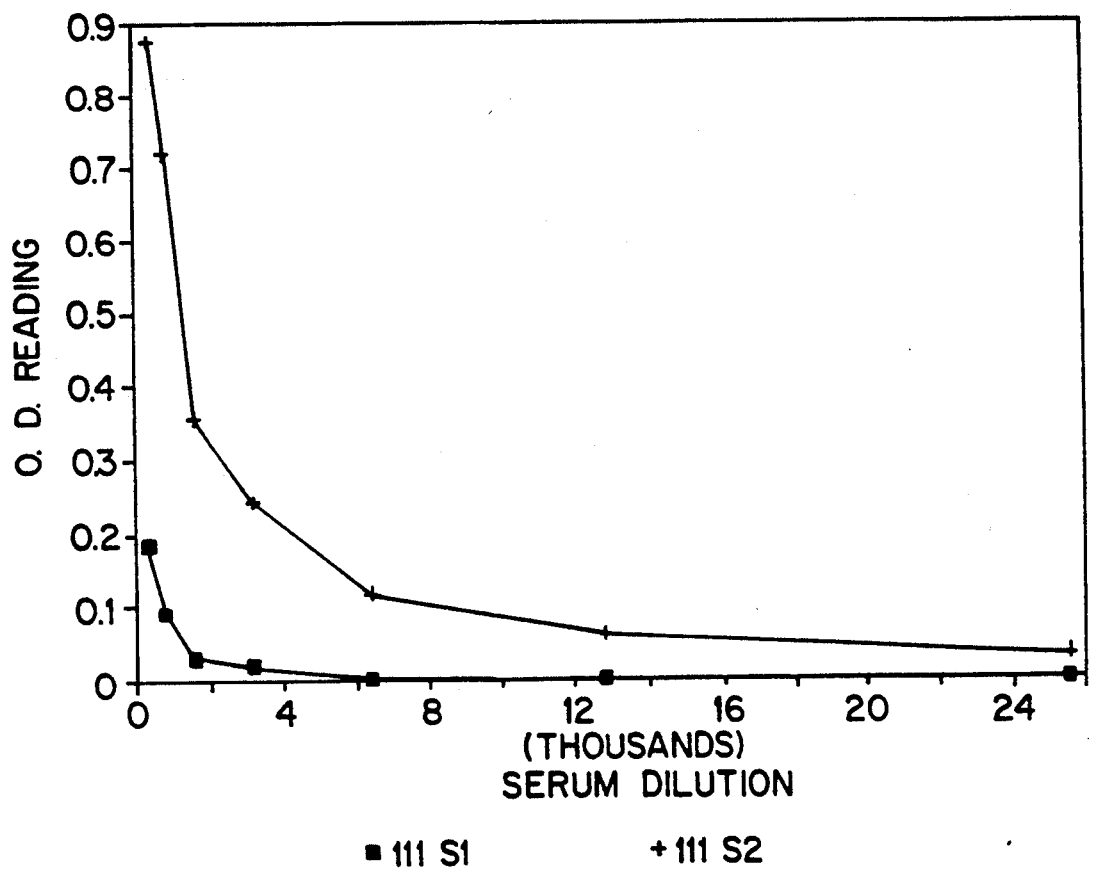
FIG. 6 shows the detection of M2-specific antibodies in human serum samples by EIA. Lysates of SF9 cells infected with the recombinant baculovirus expressing M2 were used to seed EIA plates. Plates were incubated with dilutions of either acute (111 S1) or convalescent (111 S2) phase serum. Bound antibody was detected by horse radish peroxidase conjugated Protein A.

It has been shown previously that antigens produced by recombinant baculoviruses do not have to be rigorously purified before being used in EIA tests to detect antibody specific for viral components. With the construction of Bac-M2, it was now possible to test serum samples from humans that were infected with influenza for antibody specific for the M2 protein. Such tests were impossible without an adequate source of M2 antigen. Glycine lysates were prepared from infected Sf9 cells and used to prepare EIA plates. A series of acute and convalescent phase serum pairs from individuals having influenza infection were tested. Several of the pairs show a significant increase in titer against M2 following infection (FIG. 6). The degree of the titer rise against M2 varied between serum pairs and did not always correlate with the degree of antibody titer rise against other influenza NP antigens (Table 1). The serum samples were also tested in Western blot assay to confirm that M2 was the target antigen. FIG. 7 shows that S1 serum did not react with the M2 antigen while S2 serum from influenza A infected individuals react quite strongly with M2. Neither S1 or S2 serum specimens from an individual infected with influenza B reacted with the M2 antigen in Western blot (FIG. 7) or EIA. These data indicate that the M2 protein is a target of the immune response against influenza.

EXAMPLE 4

Figure 8:
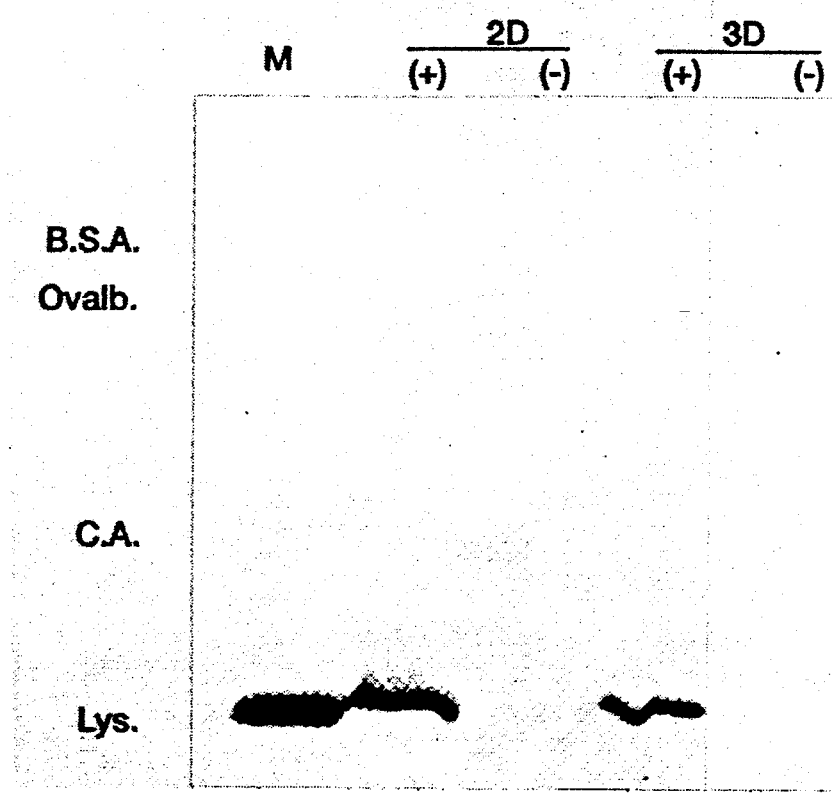
FIG. 8 demonstrates the effect of amantadine on M2 protein expression detected by Western blot. SF9 cells growing in T-150 flasks were infected with 1ml of recombinant baculovirus (about $3 \times 10^7$ pfu) were harvested at different times after infection and cells recovered by low speed centrifugation. After disruption by heating in electrophoresis sample buffer containing SDS and mercaptoethanol, aliquots were applied to 17% acrylamide gels containing 4M urea and electrophoresed until marker dye reached the end of the gel. Gels were transblotted onto nitrocellulose filters, and the presence of M2 protein detected by staining with a monoclonal antibody. M="Rainbow marker" proteins; lysozyme (lys), carbonic anhydrase (C.A.), ovalbumin (ovalb), and bovine serum albumin (BSA). 2D, 3D, =cells harvested 2 and 3 days after infection with recombinant baculovirus AA-M2-S. Cells were maintained with (+) or without(−) 2μg/ml of amantadine.
Figure 9:
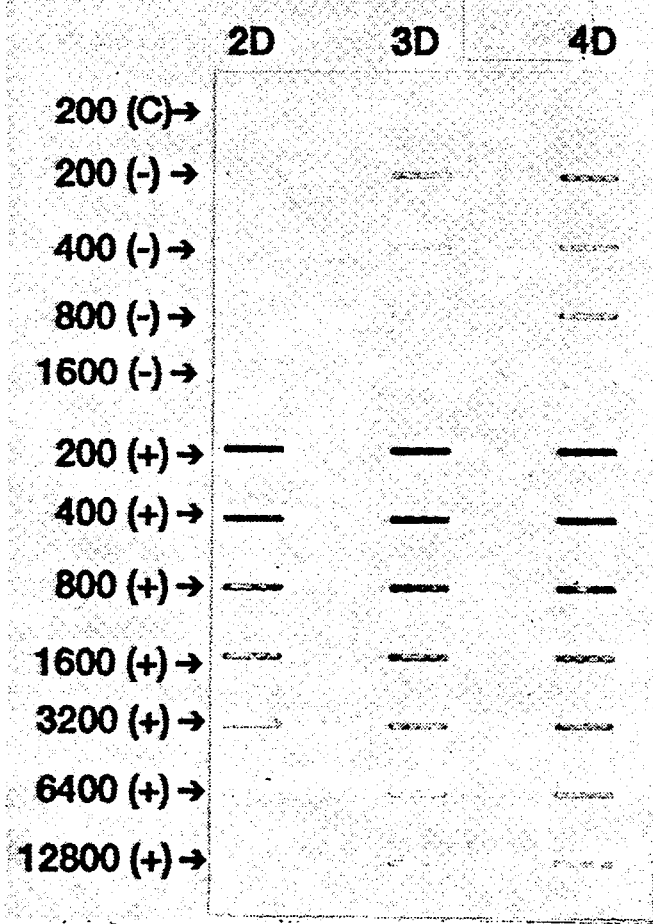
FIG. 9 represents the quantitation of M2 protein expression by slot blot analysis. Cells were infected as for FIGS. 8, and after recovery and washing in PBS disrupted by addition of 1ml of 6M guanidinium chloride in 0.1M Tris/HCl pH 7.8 buffer. Samples were diluted serially in this solution, and 50 μl aliquots then applied to nitrocellulose filter supported in a slot blot apparatus. They were immediately washed with PBS containing 0.5% Tween 20, blocked with 3% bovine serum albumin in PBS-Tween solution, and M2 protein detected with monoclonal antibody to M2 protein, followed by biotinylated sheep anti-mouse Ig, and streptavidin peroxidase A. Color was developed by soaking the filter in PBS containing 4-chloro-1-napthol (0.5 mg/ml). Columns 2D, 3D, 4D are samples of cells harvested 2, 3, and 4 days post-infection respectively. Dilutions of 1/200 up to 1/12800 were used for cells maintained after infection with (+) without (−) 2μg/ml of amantadine. A 1/200 dilution of uninfected cells was used as a control (c).

M2 protein in BAC-M2 infected cells was detected in Western blots, and the amounts of the protein were considerably greater when amantadine was included in the cell culture medium at $2\mu g/ml$ (FIG. 8). A slot blot assay was developed to better quantitate the effect of amantadine on production of M2 protein. Infected cells were lysed with 6M Guanidinium Chloride, and dilutions prepared in this reagent were applied to nitrocellulose filters. M2 protein was detected with the M2 specific monoclonal antibody C14, biotin-conjugated anti-mouse antibody, and avidin-peroxidase (Amersham). The concentration of M2 protein was at approximately 16x greater in the case of the cells maintained in the presence of amantadine (FIG. 2). This observation was repeated in numerous experiments.

All publications mentioned hereinabove are hereby incorporated by reference.

While the foregoing invention has been described in some detail for purposes of clarity and understanding, it will be appreciated by one skilled in the art from reading of this disclosure that various changes in form and detail can be made without departing from the true scope of the invention.

TABLE 1

Detection of Antibody to Influenza M2 Protein in Human Sera

| Source[1] | Virus[2] | HI[3] S2/S1 | ANP[4] P/N | BNP[5] P/N | AM2[6] P/N |
|---|---|---|---|---|---|
| Geratric | | | | | |
| 1 | A/H3 | 1280/160 | 4.1 | 1.0 | 0.8 |
| 2 | | 160/160 | 2.3 | 0.8 | 0.8 |
| 3 | | 160/84 | 2.7 | 1.2 | 5.4 |
| 4 | | 640/640 | 2.4 | 1.4 | 1.3 |
| 5 | | 640/160 | 3.9 | 1.7 | 2.4 |
| 6 | | 1280/1280 | 1.7 | NO | 1.5 |
| 7 | | 320/40 | 3.9 | NO | 0.5 |
| Students | | | | | |
| 10 | A/H3 | 320/80 | 14.0 | 1.9 | 0.9 |
| 20 | | 640/160 | 1.7 | 0.8 | 1.4 |
| 30 | | 160/160 | 4.5 | 1.1 | 2.8 |
| 40 | | 320/160 | 4.2 | 1.1 | 8.4 |
| 50 | | 320/80 | 2.7 | 0.6 | 1.5 |
| 70 | | 320/160 | 1.1 | 1.0 | 1.7 |
| 80 | | 160/10 | 1.9 | 1.3 | 2.2 |
| 106 | | 640/160 | 8.3 | 1.2 | 0.8 |
| 109 | | 320/80 | 3.0 | 1.3 | 0.6 |
| 110 | | 640/160 | 5.0 | 0.8 | 0.5 |
| 111 | | 160/160 | 7.2 | 0.9 | 8.6 |
| 90 | B | | 0.5 | 20 | 0.7 |
| 101 | | | 1.5 | 5.8 | 1.0 |
| 102 | | | 1.5 | 19 | 0.8 |

TABLE 1-continued

Detection of Antibody to Influenza M2 Protein in Human Sera

| Source[1] | Virus[2] | HI[3] S2/S1 | ANP[4] P/N | BNP[5] P/N | AM2[6] P/N |
|---|---|---|---|---|---|
| 107 | | | 0.7 | 20 | 0.7 |

Footnotes
[1]Source = patients, ill with influenza as previously proven by virus isolation or serology
[2]Virus = previously identified infecting strain
[3]HI = hemagglutin inhibition titer in convalescent phase (S2) or acute phase (S1) sera
[4]ANP = Elisa antibody titer vs Bacculovirus expressed NP antigen (P/N ratio of optical density for S2 to S1 at highest dilution of sera when S1 had O.D. >0.100; greater than 2.0 indicates positive serological response)
[5]BNP = Elisa antibody titer vs. FluB nucleoprotein (P/N ratio same as ANP)
[6]AM2 = Elisa antibody titer vs Baculovirus expressed M2 protein (P/N ratio same as ANP)

What is claimed is:

1. A composition comprising an insect cell and culture medium:
   i) said cell infected with a recombinant *Autographa Californica* nuclear polyhedrosis virus or a related nuclear polyhedrosis virus, said recombinant virus encoding the gene for an M2 protein of influenza A virus, and
   ii) wherein the medium comprises amantadine or an amantadinelike drug.

2. The composition of claim 1 wherein the medium comprises amantadine.

3. The composition of claim 1 wherein said insect cell is a *spodoptera frugiperda* cell.

4. The composition of claim 1 wherein said gene for an M2 protein of influenza A virus is operably linked to a polyhedron gene promoter.

5. The composition of claim 3 wherein said insect cell is an Sf9 cell of *Spodoptera frugiperda*.

6. The composition of claim 4 wherein said recombinant virus is *Autographa californica* nuclear polyhedrosis virus (AcNPV).

7. A method of expressing high levels of an influenza A M2 protein in an insect cell, said method comprising:
   i) infecting insect cells in the presence of amantadine or an amantadine-like drug with a recombinant *Autographa californica* nuclear polyhedrosis virus or a related nuclear polyhedrosis virus, said recombinant virus containing the gene for an M2 protein of influenza A virus, and
   ii) culturing said infected insect cells in the presence of amantadine or amantadine-like drug so as to express said M2 protein of influenza A virus.

8. The method of claim 7 wherein said infecting takes place in the presence of amantadine.

9. The method of claim 7 wherein said insect cells are *Spodoptera frugiperda* cells.

10. The method of claim 7 wherein said gene for an M2 protein of influenza A virus is operably linked to al polyhedron gene promoter.

11. The method of claim 9 wherein said insect cells are Sf9 cells of *spodoptera frugiperda*.

12. The method of claim 10 wherein said recombinant virus is *Autographa californica* nuclear polyhedrosis virus (AcNPV).

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Influenza A/Ann Arbor/6/60 virus ( i x ) FEATURE:
        ( A ) NAME/KEY: miscfeature
        ( B ) LOCATION: 1..25
        ( D ) OTHER INFORMATION: /function="PCR AMPLIFICATION"
            / product="PRIMER"
            / standardname="Primer M2F mRNA sense"

( x i ) SEQUENCE DESCRIPTION: SEQ ID NO:1:

GATCGGATCC AAGATGAGTC TTCTA        25

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( v i ) ORIGINAL SOURCE:
        ( A ) ORGANISM: Influenza A/Ann Arbor/6/60 virus ( i x ) FEATURE:
        ( A ) NAME/KEY: miscfeature
        ( B ) LOCATION: 1..25
        ( D ) OTHER INFORMATION: /function="PCR AMPLIFICATION"
            / product="PRIMER"
            / standardname="Primer M2R Reverse-complement"

( x i ) SEQUENCE DESCRIPTION: SEQ ID NO:2:

GATCAGATCT TTACTCCAGC TCTAT        25